United States Patent
Matsumasa et al.

(10) Patent No.: US 10,810,552 B2
(45) Date of Patent: Oct. 20, 2020

(54) CLINICAL PATHWAY MANAGEMENT DEVICE

(71) Applicant: FUJIFILM Corporation, Tokyo (JP)

(72) Inventors: Hironori Matsumasa, Tokyo (JP); Satoshi Ueda, Tokyo (JP); Yuya Kudo, Tokyo (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1219 days.

(21) Appl. No.: 15/086,435

(22) Filed: Mar. 31, 2016

(65) Prior Publication Data

US 2016/0210421 A1 Jul. 21, 2016

Related U.S. Application Data

(63) Continuation of application No. PCT/JP2014/075807, filed on Sep. 29, 2014.

(30) Foreign Application Priority Data

Oct. 3, 2013 (JP) ................. 2013-208214

(51) Int. Cl.
*G06Q 10/10* (2012.01)
*G06Q 50/22* (2018.01)
(Continued)

(52) U.S. Cl.
CPC ..... *G06Q 10/105* (2013.01); *G06Q 10/06313* (2013.01); *G06Q 50/22* (2013.01); *G16H 40/20* (2018.01)

(58) Field of Classification Search
CPC ................. G06Q 50/22–24; G06Q 10/105
See application file for complete search history.

(56) References Cited

U.S. PATENT DOCUMENTS

| | | | | |
|---|---|---|---|---|
| 5,946,659 A | * | 8/1999 | Lancelot ................ | G06Q 10/06 705/3 |
| 2002/0147135 A1 | * | 10/2002 | Schnell .................. | G06Q 50/24 705/3 |

(Continued)

FOREIGN PATENT DOCUMENTS

JP 2005-157560 A 6/2005

OTHER PUBLICATIONS

European Office Communication for European Application No. 14850909.4, dated Nov. 3, 2016.
(Continued)

*Primary Examiner* — Robert A Sorey
(74) *Attorney, Agent, or Firm* — Birch, Stewart, Kolasch & Birch, LLP

(57) ABSTRACT

In the clinical pathway management device, if a request for change that requires the change of the content of a clinical pathway is received, with reference to schedule data, it is determined whether or not there is an overlap between hospital resources assigned to a treatment included in a clinical pathway as a target of change and hospital resources assigned to a treatment included in other clinical pathways different from the clinical pathway as a target of change in a case where the clinical pathway is changed according to the request for change. In a case where there is no overlap, the clinical pathway is changed according to the request for change. In a case where there is an overlap because of the change of at least either the clinical pathway as a target of change or other clinical pathways described above, plural kinds of plans of change for avoiding the overlap are generated. Thereafter, a degree of influence, which is obtained by numerically expressing an extent of change made according to each of the plans of change, of each of the plans of change is calculated. Then, the clinical pathway is
(Continued)

changed according to a plan of change with a minimal degree of influence.

10 Claims, 11 Drawing Sheets

(51) Int. Cl.
G06Q 10/06 (2012.01)
G16H 40/20 (2018.01)

(56) References Cited

U.S. PATENT DOCUMENTS

| | | | | |
|---|---|---|---|---|
| 2006/0178913 A1* | 8/2006 | Lara | ............... | G16H 40/20 |
| | | | | 705/3 |
| 2008/0021834 A1 | 1/2008 | Holla et al. | | |
| 2010/0191071 A1* | 7/2010 | Anderson | ............. | G06Q 10/10 |
| | | | | 600/301 |
| 2010/0191100 A1* | 7/2010 | Anderson | ............. | A61B 5/055 |
| | | | | 600/424 |
| 2011/0166873 A1* | 7/2011 | Griffin | ................. | G06Q 10/10 |
| | | | | 705/2 |
| 2011/0196804 A1 | 8/2011 | Sutter et al. | | |
| 2013/0185310 A1* | 7/2013 | De Guise | ............ | G06F 17/5009 |
| | | | | 707/748 |
| 2013/0226601 A1* | 8/2013 | Razmi | ................ | G06F 19/3418 |
| | | | | 705/2 |
| 2016/0210417 A1* | 7/2016 | Kudo | ..................... | G06Q 50/22 |

OTHER PUBLICATIONS

"Computer network," Wikipedia, XP055117444, obtained from http://en.wikipedia.org/w/index.php?title=Computer_network&oldid=341100015, Jan. 31, 2010, 9 pages.
Extended European Search Report, dated Jun. 1, 2016, for European Application No. 14850909.4.
International Search Report for PCT/JP2014/075807 (PCT/ISA/210) dated Dec. 22, 2014.
Written Opinion of the International Searching Authority for PCT/JP2014/075807 (PCT/ISA/237) dated Dec. 22, 2014.

* cited by examiner

FIG. 4

○× OPERATION: CLINICAL PATHWAY

PATIENT'S NAME: MR. TARO FUJI
NAME OF FAMILY: MR. DAISUKE FUJI (RELATIONSHIP: FATHER)

ATTENDING DOCTOR: JIRO TANAKA
NURSE: HANAKO SUZUKI

| DATE | | 9/14 | 9/15 | 9/16 | 9/17 |
|---|---|---|---|---|---|
| GOAL | | UNDERSTANDING OPERATION | MENTALLY AND PHYSICALLY PREPARED | NO HEMORRHAGE | ABLE TO WALK |
| EVENT | | HOSPITALIZATION — [PRELIMINARY EXAMINATION] — DINNER (SPECIAL DIET) ← BREAKFAST (SPECIAL DIET) | ○× OPERATION | ← INFUSION → | ← REHABILITATION → DISCHARGE ↑ BREAKFAST (NORMAL DIET) |
| DIET | | LUNCH (NORMAL DIET) | | | |
| PLACE | | A ROOM (FROM 10:00) B EXAMINATION ROOM (12:00 TO 13:00) | A ROOM (24 HOURS) C OPERATING ROOM (13:00 TO 15:00) | A ROOM (24 HOURS) | A ROOM (TO 12:00) D REHABILITATION ROOM (10:00 TO 11:00) |
| STAFF | | EXAMINATION TECHNICIAN B (12:00 TO 13:00) | OPERATION STAFF A (13:00 TO 15:00) OPERATION STAFF B (13:00 TO 15:00) ANESTHETIST A (13:00 TO 15:00) | JIRO TAKANA (24 HOURS) HANAKO SUZUKI (24 HOURS) | REHABILITATION STAFF D (10:00 TO 11:00) |

THE ABOVE CONTENT IS APPROVED ●YES ○NO
A DIGITAL SIGNATURE SYSTEM CERTIFIES THAT THE ABOVE APPROVAL IS OBTAINED FROM MR. DAISUKE FUJI (RELATIONSHIP: FATHER OF PATIENT).
∗ A CERTIFICATE IS ISSUED BY CLICKING THE EFFECTIVE BUTTON ON THE RIGHT-HAND SIDE. [ISSUE CERTIFICATE]

FIG. 5

| USER'S NAME | USER ID | TERMINAL ID | CONTACT | ATTRIBUTE |
|---|---|---|---|---|
| GORO YAMADA | 3651 | CDBA | PHONE 32-3456-7890 E-MAIL 323@456.ne.jp | DOCTOR DEPARTMENT: FIRST DEPARTMENT OF SURGERY POSITION: CHIEF |
| JIRO TANAKA | 1234 | ABCD | PHONE 12-3456-7890 E-MAIL 123@456.ne.jp | DOCTOR DEPARTMENT: FIRST DEPARTMENT OF SURGERY POSITION: VICE CHIEF |
| HANAKO SUZUKI | 1235 | ABCE | PHONE 92-3456-7890 E-MAIL 923@456.ne.jp | NURSE DEPARTMENT: FIRST DEPARTMENT OF SURGERY POSITION: CHIEF NURSE |
| OPERATION STAFF A | 1236 | ABCF | PHONE 62-3456-7890 E-MAIL 623@456.ne.jp | OPERATION STAFF DEPARTMENT: FIRST DEPARTMENT OF SURGERY POSITION: ASSISTANT |
| ⋮ | ⋮ | ⋮ | ⋮ | ⋮ |

28 USER INFORMATION

FIG. 6

| HOSPITAL RESOURCES | OPERATION SCHEDULE ||||
|---|---|---|---|---|
| | SEPTEMBER 14 | SEPTEMBER 15 | | SEPTEMBER 16 |
| | ... | 06:00  10:00  14:00  18:00  22:00 | | ... |
| HUMAN RESOURCES | | | | |
| GORO YAMADA | ... | OPERATION   OPERATION | | ... |
| JIRO TANAKA | ... | OPERATION   OPERATION | | ... |
| ⋮ | ⋮ | ⋮ | | ⋮ |
| MATERIAL RESOURCES | | | | |
| SPACE | | | | |
| OPERATING ROOM A | ... | USED   USED | | ... |
| EXAMINATION ROOM A | ... | USED USED   USED USED | | ... |
| ⋮ | ⋮ | ⋮ | | ⋮ |
| EQUIPMENT | | | | |
| SURGICAL INSTRUMENT A | ... | USED   USED | | ... |
| EXAMINATION INSTRUMENT A | ... | USED USED   USED USED | | ... |
| ⋮ | ⋮ | ⋮ | | ⋮ |

29 SCHEDULE DATA

FIG. 11

| | ATTRIBUTE | WEIGHTING COEFFICIENT | ~110 |
|---|---|---|---|
| DOCTOR | SURGEON | 10 | |
| | PHYSICIAN | 8 | |
| | RADIOLOGIST | 8 | |
| | MEDICAL ONCOLOGIST | 7 | |
| | PATHOLOGIST | 8 | |
| | PALLIATIVE CARE DOCTOR | 8 | |
| | PSYCHO-ONCOLOGIST | 6 | |
| | REHABILITATION DOCTOR | 6 | |
| | ANESTHETIST | 9 | |
| | ⋮ | ⋮ | |
| STAFF OTHER THAN DOCTOR | NURSE | 6 | |
| | CLINICAL EXAMINATION TECHNICIAN | 4 | |
| | PHARMACIST | 4 | |
| | DIETITIAN | 3 | |
| | PHYSIOTHERAPIST | 3 | |
| | OCCUPATIONAL THERAPIST | 3 | |
| | SPEECH-HEARING THERAPIST | 3 | |
| | ORTHOPTIST | 5 | |
| | MEDICAL RADIOLOGY TECHNICIAN | 4 | |
| | MEDICAL SOCIAL WORKER | 3 | |
| | HEALTH INFORMATION MANAGER | 3 | |
| | CYTOTECHNOLOGIST | 3 | |
| | CLINICAL ENGINEER | 2 | |
| | ⋮ | ⋮ | |

FIG. 12

| AUTHORITY LEVEL | WEIGHTING COEFFICIENT | ~120 |
|---|---|---|
| 5 | 5 | |
| 4 | 4 | |
| 3 | 3 | |
| 2 | 2 | |
| 1 | 1 | |

FIG. 13

| OPERATION RATIO(%) | WEIGHTING COEFFICIENT |
|---|---|
| EQUAL TO OR GREATER THAN 80 | 5 |
| EQUAL TO OR GREATER THAN 60 BUT LESS THAN 80 | 4 |
| EQUAL TO OR GREATER THAN 40 BUT LESS THAN 60 | 3 |
| LESS THAN 40 | 2 |

| MODALITY | NUMBER OF DEVICE OWNED | OPERATION RATIO(%) | WEIGHTING COEFFICIENT |
|---|---|---|---|
| CT | 5 | 65 | 4 |
| MRI | 5 | 83 | 5 |
| PET | 2 | 72 | 4 |
| MAMMOGRAPHY | 3 | 60 | 3 |
| ULTRASONOGRAPH | 10 | 55 | 3 |
| ⋮ | ⋮ | ⋮ | ⋮ |
| BONE MINERAL CONTENT EXAMINATION DEVICE | 1 | 90 | 5 |

| ITEM OF CHANGE | WEIGHTING COEFFICIENT |
|---|---|
| CHANGE OF TREATMENT CONTENT | 5 |
| CHANGE OF STAFF | 4 |
| CHANGE OF MEDICAL INSTRUMENT | 3 |

~150

CLINICAL PATHWAY MANAGEMENT DEVICE

CROSS-REFERENCE TO RELATED APPLICATIONS

This application is a Continuation of PCT International Application No. PCT/JP2014/075807 filed on Sep. 29, 2014, which claims priority under 35 U.S.C § 119(a) to Japanese Patent Application No. 2013-208214 filed Oct. 3, 2013. The above application is hereby expressly incorporated by reference, in its entirety, into the present application.

BACKGROUND OF THE INVENTION

1. Field of the Invention

The present invention relates to a clinical pathway management device for managing clinical pathways.

2. Description Related to the Prior Art

In recent years, the introduction of clinical pathways has been increasingly accelerated in medical institutions. A clinical pathway is a scheme showing the plan of treatment (therapy, examination, or the like) for a patient. By visualizing the treatment plan by means of creating the clinical pathway, in medical institutions, medical staff such as doctors or nurses can share information, and steady high-quality treatments can be provided. Furthermore, patients can receive treatments with peace of mind after understanding the treatment plan.

The clinical pathway shows the treatment plan that is made at the point in time when the pathway is created. Therefore, for example, in some cases, the pathological conditions of the patient are less serious or more serious than expected at the point in time when the clinical pathway is created. That is, there is a difference between the situation at the point in time when the clinical pathway is created and the current situation in some cases. In this case, the clinical pathway needs to be appropriately changed according to the current situation.

At the time of creating the clinical pathway, according to the date and time when treatments are to be performed, hospital resources necessary for performing the treatments are assigned to each of the treatments. The hospital resources include not only material resources such as a patient room, a treatment room, an operating room, medical instruments such as examination instruments and therapeutic instruments but also human resources such as medical staff, specifically, doctors, nurses, and examination technicians. In a case where the clinical pathway is changed, the contents of the treatment or the date and time when treatments are to be performed are changed, and as a result, the hospital resources for the treatment need to be reassigned according to the change.

As a technique considering the aforementioned change of the clinical pathway, for example, JP2005-157560A described below is known. In JP2005-157560A described below, at the time of changing the clinical pathway, whether or not the content of the change can be changed is determined by checking the content of the change against the schedule of the hospital resources, and in a case where the change is possible, the clinical pathway is changed. Specifically, in a case where there is a space in the schedule of the hospital resources, it is determined that the change is possible, and the clinical pathway is changed. In a case where there is no space, it is determined that the change is impossible, and the clinical pathway is not changed. Furthermore, in JP2005-157560A described below, in a case where the clinical pathway is changed, the people concerned (doctors or nurses who are influenced) are informed about the change.

As described above, the clinical pathway needs to be changed depending on the situation in some cases. However, in a case where there is no space in the schedule of the hospital resources, it is determined that the schedule cannot be changed as a whole, and accordingly, JP2005-157560A has a problem of not being able to flexibly respond to the change. For example, in JP2005-157560A, in a case where there is a desire to add CT screening to the clinical pathway as a target of change, if there is no space in the schedule because the hospital resources (CT device, radiology technicians, and the like) necessary for performing the CT screening are assigned to other clinical pathways, it is impossible to change the clinical pathway as a whole. That is, the clinical pathway can only be changed within a range that does not exert an influence to clinical pathways other than the clinical pathway as a target of change, and hence the technique needs to be further improved in terms of flexibility.

SUMMARY OF THE INVENTION

An object of the present invention is to provide a clinical pathway management device that can respond flexibly to a change of a clinical pathway.

In order to achieve the aforementioned object, a clinical pathway management device of the present invention comprises a database, a reception portion, an overlap determination portion, a change plan generation portion, an influence degree calculation portion, and a clinical pathway changing portion. The database stores a plurality of clinical pathways showing treatment plans designed for each patient and schedule data showing operation schedules of hospital resources which are assigned to each treatment in each clinical pathway and include at least either human resources or material resources. The reception portion receives a request for change for changing at least either content of the treatment or date and time of performing the treatment in a clinical pathway. In a case where a clinical pathway as a target of change is changed according to the request for change, the overlap determination portion determines whether or not there is an overlap between the hospital resources assigned to a treatment included in a clinical pathway as the target of change and the hospital resources assigned to a treatment included in other clinical pathways different from the clinical pathway as the target of change. In a case where there is an overlap, the change plan generation portion generates plural kinds of plans of change for avoiding the overlap by changing at least either the clinical pathway as the target of change or other clinical pathways. The influence degree calculation portion calculates a degree of influence showing an extent of change made according to each of the plural kinds of plans of change. The clinical pathway changing portion is a portion which changes clinical pathways. In a case where there is no overlap, the clinical pathway changing portion changes the clinical pathway according to the request for change, and in a case where there is an overlap, the clinical pathway changing portion changes the clinical pathway according to a plan of change determined based on the degree of influence.

It is preferable that the clinical pathway management device of the present invention further comprises an automatic selection portion which automatically selects a plan of change with a minimal degree of influence by comparing degrees of influence of the respective plans of change. It is preferable that the clinical pathway changing portion changes the clinical pathway based on the plan of change selected by the automatic selection portion.

The clinical pathway management device of the present invention may further comprise a manual selection portion which allows a user to determine which of the plans of change is to be adopted by delivering a plan selection screen including the content of each of the plans of change and the degree of influence of each of the plans of change to a terminal of the user. The clinical pathway changing portion may change a clinical pathway based on a plan of change selected through the manual selection portion.

It is preferable that the influence degree calculation portion calculates the degree of influence based on parameters.

It is preferable that the parameters include treatment costs that change with the change of the clinical pathway.

It is preferable that the parameters include the number of patients of other clinical pathways influenced by the change of the clinical pathway as the target of change.

It is preferable that the parameters include the number of medical staff as human resources influenced by the change of the clinical pathway.

In the clinical pathway management device of the present invention, weighting coefficients for performing weighting according to attributes of the medical staff to be changed are set. It is preferable that the influence degree calculation portion calculates the degree of influence based on the number of the medical staff and the weighting coefficients corresponding to the attributes.

It is preferable that the parameters include the number of medical instruments as material resources influenced by the change of the clinical pathway.

The influence degree calculation portion may calculate the degree of influence by using, as the parameters, the number of medical instruments whose operation schedule is changed according to the change of the clinical pathway.

In the clinical pathway management device of the present invention, weighting coefficients for performing weighting according to operation ratios of the medical instruments are set. It is preferable that the influence degree calculation portion calculates a degree of influence based on the number of medical instruments and the weighting coefficients corresponding to the operation ratios.

It is preferable that the influence degree calculation portion stores the parameters and calculates the degree of influence as a degree of individual influence of each technique by using a plurality of techniques different from each other in terms of at least one of the parameters. Furthermore, in the influence degree calculation portion, a weighting coefficient for performing weighting according to the techniques is set. It is preferable that the influence degree calculation portion calculates a degree of comprehensive influence based on the degree of individual influence of each technique and the weighting coefficient of each technique.

In the present invention, in order to respond to the change of a single clinical pathway, a case where other clinical pathways different from the above clinical pathway are also changed is taken into consideration. Therefore, clinical pathways can be flexibly changed. Furthermore, in the present invention, when a plurality of clinical pathways is changed as described above, a plurality of patterns of plans of change is created, and each of the plans of change is changed to a plan of change selected in consideration of the degree of influence exerted on other clinical pathways. Accordingly, the plan of change can be changed to a more appropriate plan of change.

BRIEF DESCRIPTION OF DRAWINGS

For more complete understanding of the present invention, and the advantage thereof, reference is now made to the subsequent descriptions taken in conjunction with the accompanying drawings, in which:

FIG. 4 is a view illustrating a state where a clinical pathway is displayed;

FIG. 5 is a view illustrating user information;

FIG. 6 is a view illustrating schedule data;

FIG. 11 is a view illustrating a weighting correspondence table;

FIG. 12 is a view illustrating a weighting correspondence table;

FIG. 13 is a view illustrating a weighting correspondence table;

FIG. 14 is a view illustrating operation ratios of medical instruments; and

FIG. 15 is a view illustrating a weighting correspondence table.

DESCRIPTION OF THE PREFERRED EMBODIMENTS

Figure 1:
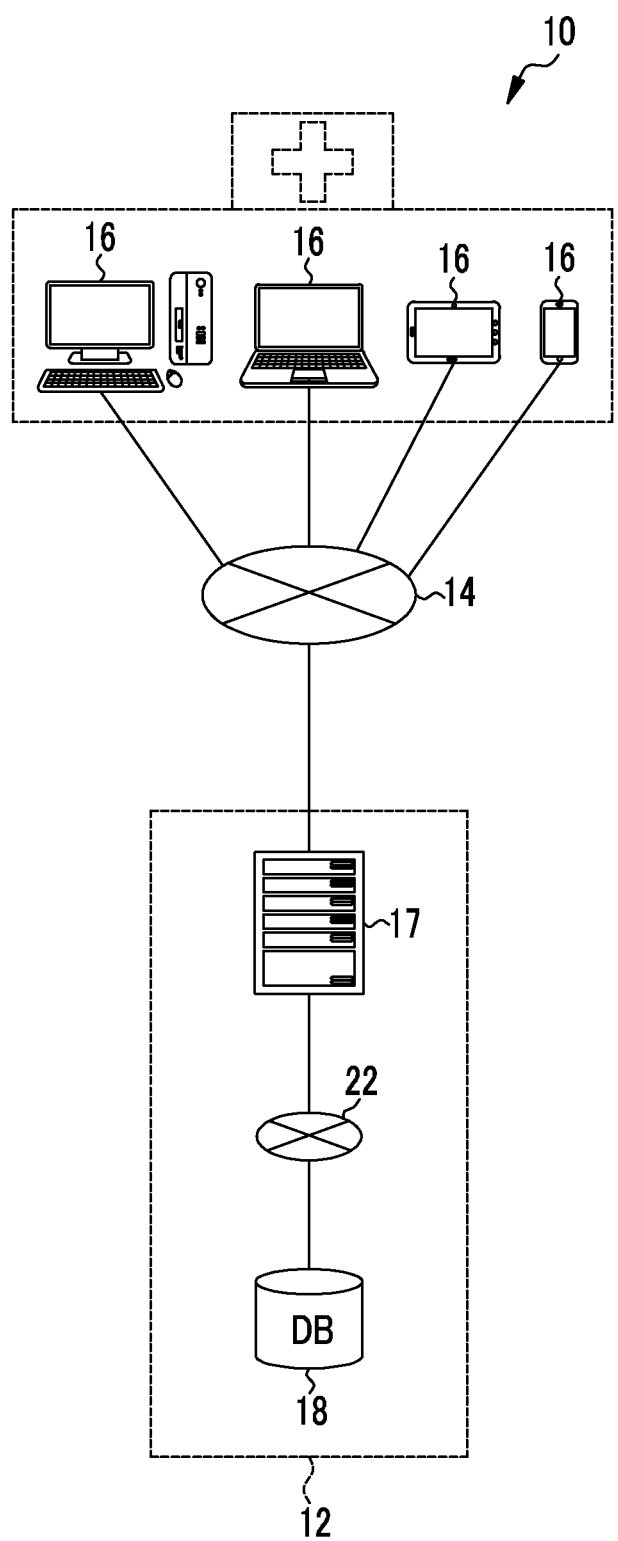
FIG. 1 is a schematic view showing a configuration of a medical care support system.

A medical care support system 10 shown in FIG. 1 is a system that supports the medical care using a clinical pathway 26 (see FIGS. 3 and 4) showing a plan of treatments (diagnosis, therapy, examination, and the like) provided to a patient, and comprises a clinical pathway management device 12 that performs the management (creation, storage, delivery, change, and the like) of the clinical pathway 26.

The clinical pathway management device 12 is connected to a plurality of user's terminals 16 of the medical care support system 10 through a network 14 such as internet. By delivering an operation screen such as Graphical User Interface (GUI) to the terminals 16 through the network 14, the clinical pathway management device 12 manages the clinical pathway 26 according to operation instructions input from the terminals 16 through the operation screen.

The terminals 16 are known electronic instruments such as desktop computers, laptop computers, tablet terminals, mobile phones, or smart phones that have a function of providing access to the network 14 and comprises input means such as a keyboard or a mouse or display means such as a liquid crystal display (alternatively, a touch panel-type display functioning as both the input means and the display means). These terminals 16 are used by users of the medical care support system 10. The users of the medical care support system 10 are medical staff such as attending doctors in charge of treating patients, nurses or examination technicians assisting the attending doctors, and the like.

The clinical pathway management device 12 is installed in, for example, an operating company that operates the medical care support system 10. The clinical pathway management device 12 is configured with an application server 17, which performs various functions such as delivery of an operation screen or management of the clinical pathway 26 according to an application preprogram (AP) 31 (see FIG. 8) that will be described later, and a database (DB) 18. The application server 17 and the DB 18 are connected to each other through a network 22 such as LAN.

Figure 2:
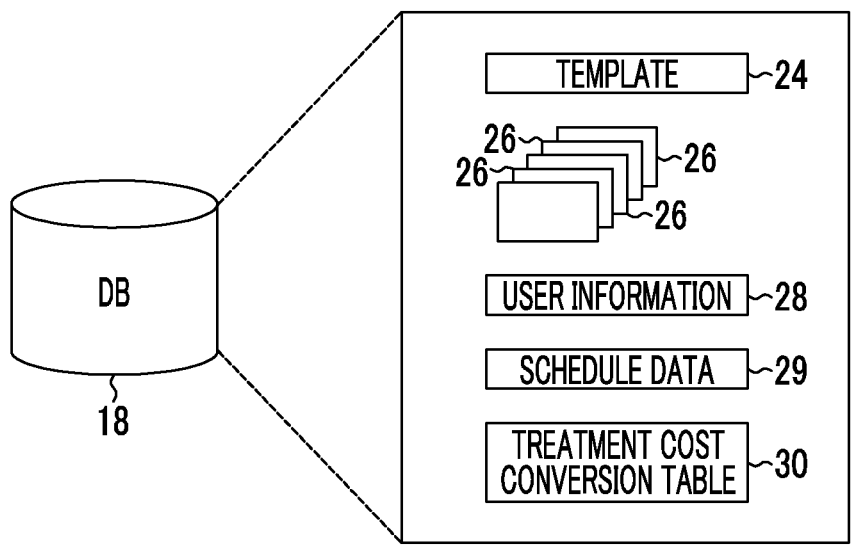
FIG. 2 is a view illustrating data stored in a database.
Figure 7:
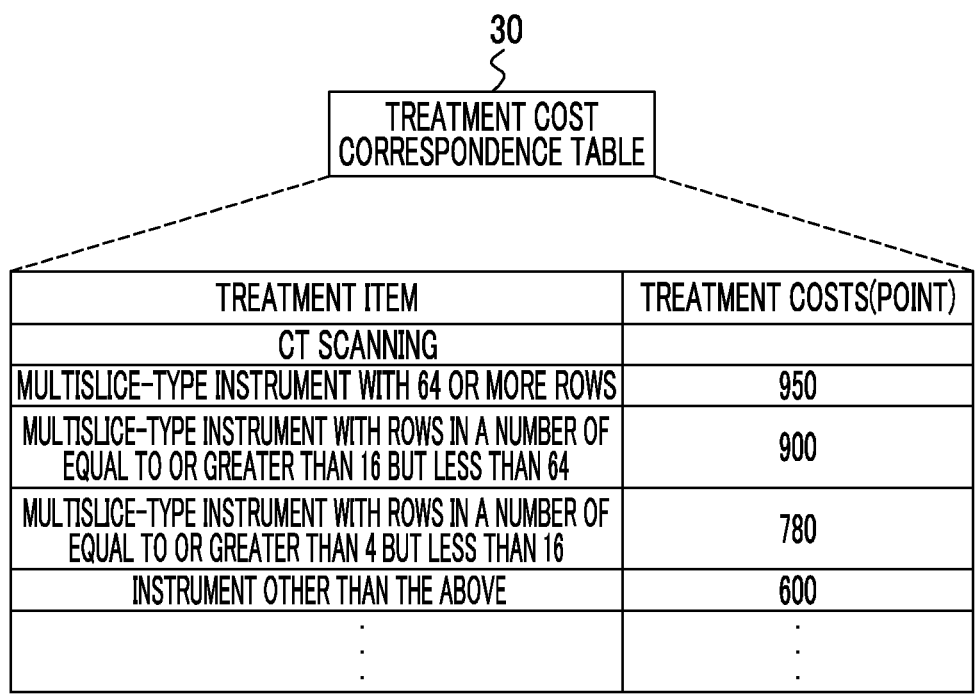
FIG. 7 is a view illustrating a treatment cost conversion table.

As shown in FIG. 2, the DB 18 stores a template 24, the clinical pathway 26 (see FIGS. 3 and 4), user information 28 (see FIG. 5), schedule data 29 (see FIG. 6), and a treatment cost conversion table 30 (see FIG. 7). The template 24 is used as a base for newly creating the clinical pathway 26.

Figure 3:
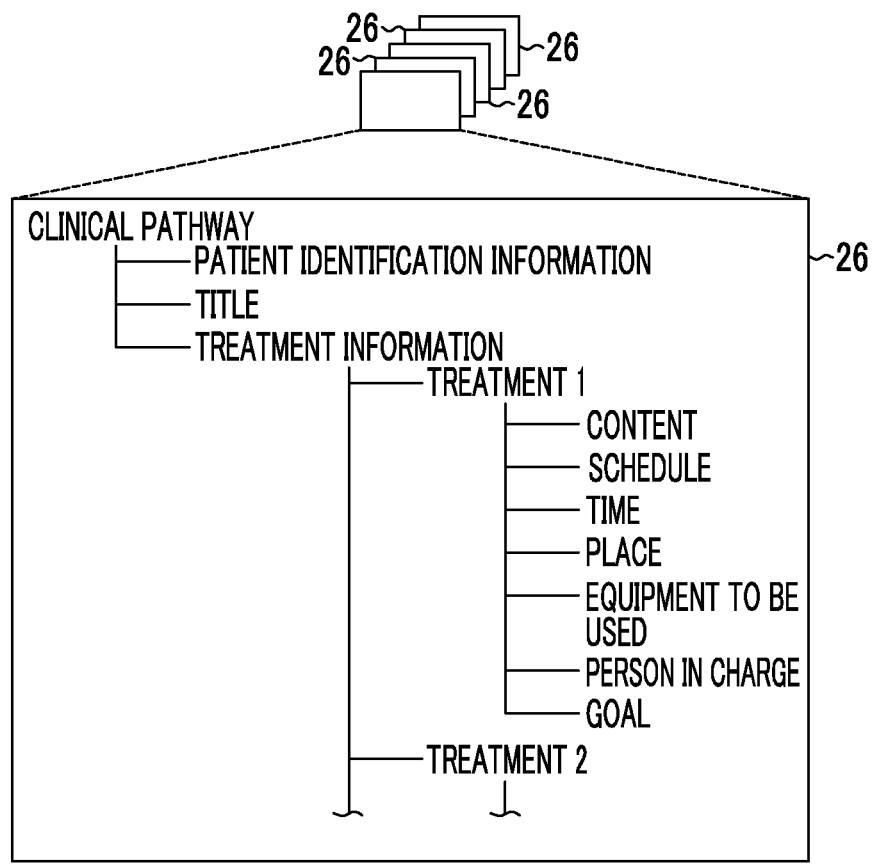
FIG. 3 is a view illustrating a data system of a clinical pathway.

As shown in FIGS. 3 and 4, in the clinical pathway 26, a treatment plan for each patient is recorded. The clinical pathway 26 includes various information such as patient identification information (patient's name or patient ID) for identifying the patient who will be provided with the treatment, the date and time when the treatment is to be performed at each stage of the clinical pathway 26, the place, the equipment to be used that is assigned to the treatment, and the medical staff. FIG. 3 shows the data system configuring the clinical pathway 26, and FIG. 4 shows a state where the clinical pathway 26 is displayed for being browsed.

As shown in FIG. 5, in the user information 28, the identification information for identifying users such as a user's name and a user ID, a terminal ID for identifying the terminal 16 the user possesses, contact information (phone number or e-mail address) of users, and attribute information (medical departments to which the user belongs, position of the user, or the like) of users are associated with each other.

The user information 28 varies between the respective users. For example, the user information about one user is generated by user registration processing performed at the time of using the medical care support system 10 for the first time and stored (newly registered) in the DB 18. In the user registration processing, a user is required to input the user's name, the contact information, and the attribute information. If the user inputs the user's name and the attribute information through the terminal 16 of the user, a user ID is assigned, and a terminal ID of the terminal 16 as an input source of information is obtained. The terminal ID is associated with the user ID together with the user's name, the contact information, and the attribute information, and as a result, the user information is generated.

As shown in FIG. 6, the schedule data 29 shows an operation schedule of each of hospital resources. The hospital resources include not only material resources such as places (spaces) like a patient room, a treatment room, and an operating room and equipment like an examination instrument, a surgical instrument, and a therapeutic instrument but also human resources such as medical staff, specifically, doctors, nurses, and examination technicians. The hospital resources are assigned according to the content of individual treatment that becomes the constituent of the clinical pathway 26 of each patient. The operation schedule is made by arranging treatments assigned for each of the hospital resources in a time series manner. The schedule data 29 stays up to date all the time by the generation of a new clinical pathway 26 or by being updated whenever the existing clinical pathway 26 is changed.

The schedule data 29 may be created or updated by a method in which a user manually inputs the operation schedule of each of the hospital resources according to a predetermined template. Furthermore, a CPU 36 (see FIG. 8) may be caused to function as a schedule data generation portion by the AP 31 (see FIG. 8) which will be described later, and the schedule data 29 may be automatically generated by the schedule data generation portion. In the clinical pathway 26, the date and time when the treatment is to be performed and the hospital resources assigned to the treatment are recorded. By reading a plurality of clinical pathways 26 out of the DB 18 and analyzing each of the clinical pathways 26, it is possible to ascertain the date and time when one hospital resource operates. By extracting the date and time of the operation of each of the hospital resources from the plurality of clinical pathways 26, the schedule data generation portion ascertains the operation schedule of each of the hospital resources and generates the schedule data 29. The schedule data generation portion may update the schedule data 29 in the same manner as described above, in addition to newly generating the schedule data 29.

As shown in FIG. 7, the treatment cost conversion table 30 shows the costs for treatments performed in medical institutions by scores and is determined by a predetermined institution (for example, Central Social Insurance Medical Council). The treatment cost conversion table 30 is used at the time of charging treatment costs to a patient or a country as an insurance carrier. In addition, as will be described later, in the present embodiment, the treatment cost conversion table 30 is also used for calculating a degree of influence exerted at the time of changing the clinical pathway 26.

Figure 8:
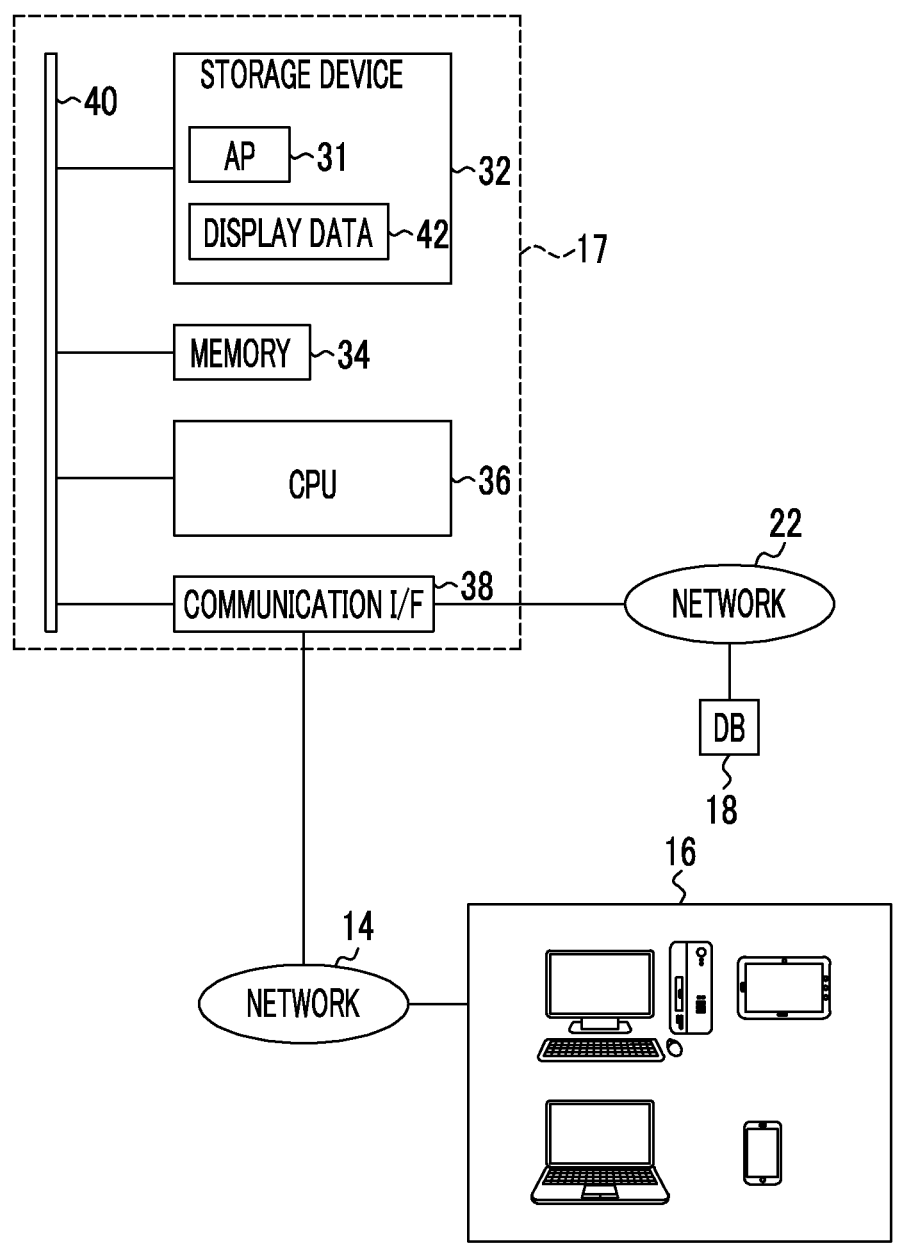
FIG. 8 is a block diagram showing a configuration of an application server.

As shown in FIG. 8, the application server 17 has a configuration in which a computer such as a personal computer or a workstation is used as a base, and a control program such as an operating system or the AP 31 that is for causing the computer to function as the application server 17 is installed in the computer.

The application server 17 comprises a storage device 32, a memory 34, a CPU 36, and a communication I/F 38, and these are connected to each other through a database 40. The storage device 32 is, for example, a hard disk drive, and is a built-in internal storage embedded in the body of the application server 17. The storage device 32 stores a control program, the AP 31 such as software for the application server, images and messages displayed at the time of executing the AP 31, display data 42 for displaying various operation screens, and the like.

The memory 34 is a work memory that the CPU 36 uses for executing processing. By loading the control program stored in the storage device 32 into the memory 34 and executing processing according to the program, the CPU 36 generally controls the respective portions of the computer. The communication I/F 38 comprises interfaces for communicating with the networks 14 and 22. Via the communication I/F 38, the application server 17 communicates with the DB 18 and the terminal 16 through the networks 14 and 22.

The AP 31 is a program for causing the computer to perform various functions. By loading the AP 31 stored in the storage device 32 into the memory 34 and executing processing according to the program, the CPU 36 generally controls the respective portions of the computer.

Figure 9:
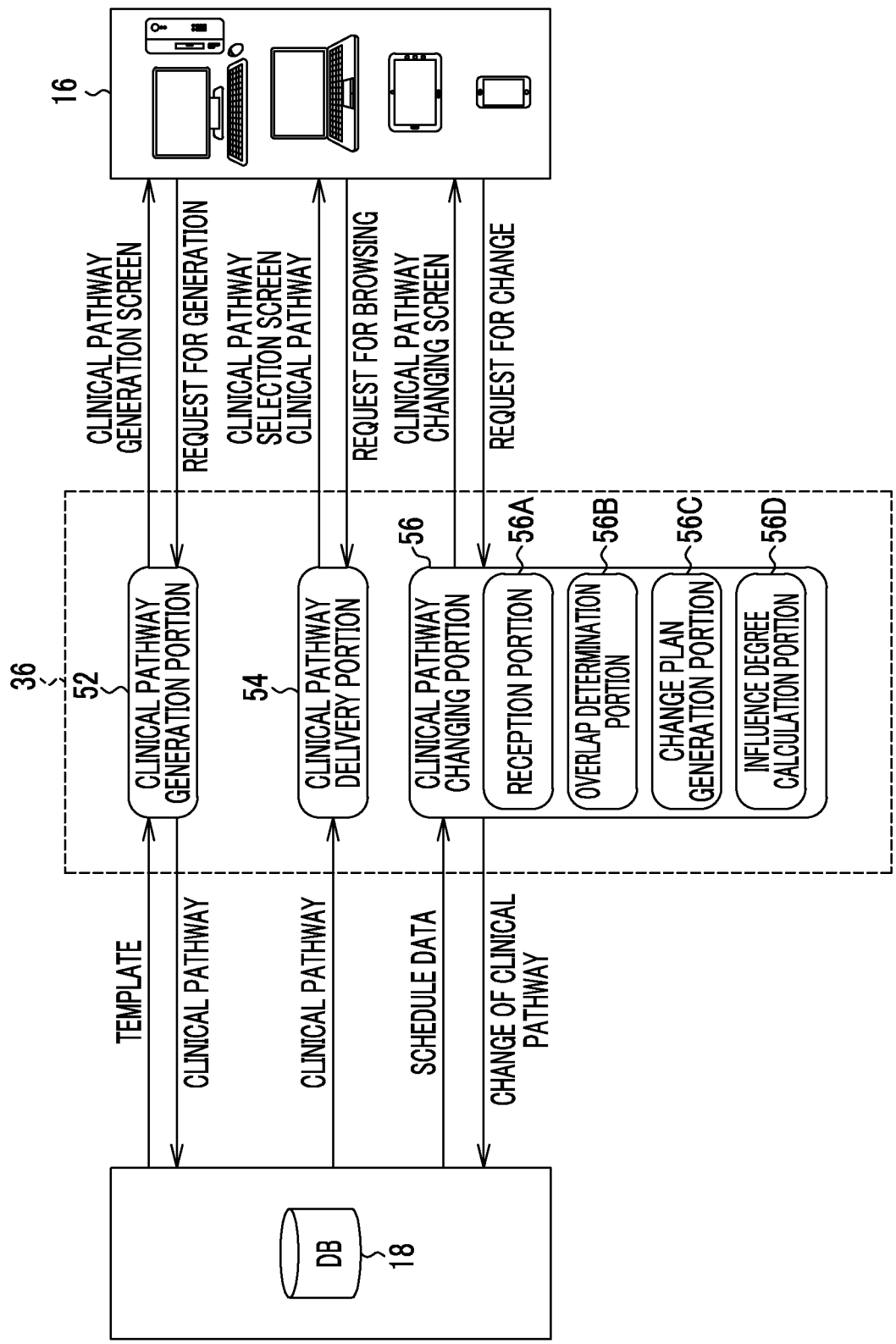
FIG. 9 is a view showing a functional configuration of the application server.

As shown in FIG. 9, when the AP 31 starts to run, the CPU 36 functions as a clinical pathway generation portion 52, a clinical pathway delivery portion 54, and a clinical pathway changing portion 56 in cooperation with the memory 34.

According to the request from the terminal 16 of a user, the clinical pathway generation portion 52 delivers a clinical pathway generation screen, which is an operation screen for generating the clinical pathway 26, to the terminal 16 of the user, and generates a new clinical pathway 26 according to the instructions from the user that are issued through the clinical pathway generation screen. According to the clinical pathway generation screen, the user selects one of the templates 24 of the clinical pathways 26 stored in the DB 18 and then inputs each processing information, which will become the constituent of the clinical pathway 26 (treatment plan) for a patient, into the selected template 24. If the user selects the template 24 and inputs the treatment information, a request for generation that requires generation of a new clinical pathway 26 according to the treatment information is input into the clinical pathway generation portion 52 from the terminal 16 of the user. Based on the request for creation of a clinical pathway, the clinical pathway generation portion 52 generates a new clinical pathway 26 and stores it into the DB 18.

The clinical pathway delivery portion 54 delivers a clinical pathway selection screen, which is an operation screen for selecting a clinical pathway 26 the user wants to browse, to the terminal 16 of the user. According to the clinical pathway selection screen, the user selects a clinical pathway 26 the user wants to browse from the clinical pathways 26 stored in the DB 18. If the user selects the clinical pathway 26, a request for browsing of the selected clinical pathway 26 is input into the clinical pathway delivery portion 54 from the terminal 16 of the user. The clinical pathway delivery portion 54 delivers the clinical pathway 26, for which the request for browsing is made, to the terminal 16 of the user.

According to the request from the terminal 16 of the user, the clinical pathway changing portion 56 delivers a clinical pathway changing screen, which is an operation screen for changing the clinical pathway 26, to the terminal 16 of the user. Furthermore, according to instructions from the user that are issued through the clinical pathway changing screen, the clinical pathway changing portion 56 changes the clinical pathways 26 stored in the DB 18. Through the clinical pathway changing screen, the user selects the clinical pathway 26 to be changed or designates the content of change including the change of at least either the treatment content or the date and time when the treatment is to be performed. The change of the treatment content and the change of the date and time when the treatment is to be performed also include the deletion or addition of treatments. If the user designates the clinical pathway 26 to be changed and the content of change, a request for change that requires the change according to the content is input into the clinical pathway changing portion 56 from the terminal 16 of the user.

Based on the request for change, the clinical pathway changing portion 56 changes the clinical pathway 26. The clinical pathway changing portion 56 comprises a reception portion 56A, an overlap determination portion 56B, a change plan generation portion 56C, and a degree of influence degree calculation portion 56D. The reception portion 56A receives the request for change of the clinical pathway 26.

With reference to the schedule data 29, the overlap determination portion 56B determines whether or not there is an overlap between the hospital resources assigned to the treatment included in the clinical pathway 26 as a target of change and the hospital resources assigned to the treatment included in other clinical pathways 26 different from the clinical pathway 26 as a target of change (hereinafter, simply referred to as other clinical pathways 26) in a case where the clinical pathway 26 as a target of change is changed according to the request for change.

The hospital resources are assigned to each treatment. However, in a case where the clinical pathway 26 is changed, the treatment content or the date and time when the treatment is to be performed are changed, and hence the hospital resources need to be reassigned according to the change. For example, in a case where the clinical pathway 26 as a target of change is changed according to the request for change, the medical staff or the examination instruments assigned to the treatment constituting the clinical pathway 26 as a target of change are assigned to the treatment constituting other clinical pathways 26 that are scheduled to be performed on the same date and time as the changed clinical pathway in some cases, and this means the overlap of the hospital resources. The overlap determination portion 56B determines whether or not there is such an overlap. In this way, because the hospital resources are related to a plurality of clinical pathways 26, if a single clinical pathway 26 is changed, other clinical pathways 26 are influenced by the change in some cases.

In a case where it is determined that there is no overlap, the clinical pathway changing portion 56 changes the clinical pathway 26 according to the request for change. In contrast, in a case where it is determined that there is an overlap, the change plan generation portion 56C generates plural kinds of plans of change for avoiding the overlap by changing at least either the clinical pathway 26 as a target of change or other clinical pathways 26. During the generation of the plans of change, the plans of change are generated by the following methods 1 to 4, for example.

[Method 1]

It is a method for generating a plan of change by changing the date and time when the treatment, which is assigned with overlapping hospital resources, is to be performed without changing the overlapping hospital resources.

For example, in a case where the same examination instrument or the same person in charge of examination is assigned to a plurality of treatments performed on the same date and time in a plurality of clinical pathways 26, by changing the date and time when one of the treatments is to be performed, a plan of change for avoiding the overlap is generated.

[Method 2]

It is a method for generating a plan of change by changing the hospital resources for one of treatments assigned with overlapping hospital resources, without changing the date and time when the overlapping hospital resources are to be operated.

For example, in a case where the same examination instrument or the same person in charge of examination is assigned to a plurality of treatments performed on the same date and time in a plurality of clinical pathways 26, by changing the examination instrument or the person in charge of examination assigned to one of the treatments, a plan of change for avoiding the overlap is generated.

[Method 3]

It is a method for generating a plan of change by changing both the overlapping hospital resources and the date and time when the treatment assigned with the hospital resources is to be performed.

For example, in a case where the same examination instrument or the same person in charge of examination is assigned to a plurality of treatments performed on the same date and time in a plurality of clinical pathways 26, by combining the method 1 with the method 2, a plan of change for avoiding the overlap is generated.

[Method 4]

It is a method for generating a plan of change by changing the content of the treatment assigned with overlapping hospital resources.

For example, in a case where the same examination instrument or the same person in charge of examination is assigned to a plurality of treatments performed on the same date and time in a plurality of clinical pathways 26, by means of change including cancellation of one of the treatments, simplification of the treatment content by the reduction of the number of examination items, replacement with other treatment contents having the same function, and the like, a plan of change for avoiding the overlap is generated.

The number of the plans of change generated by each of the aforementioned methods is not limited to one. For example, the method 1 described above may generates 2 kinds of plans of change including a plan of change in which a time difference of 1 hour is made between the dates and times to perform the overlapping treatments and a plan of change in which a time difference of 2 hours is made between the dates and times to perform the overlapping treatments. Furthermore, the plan of change may be generated by using the aforementioned methods in combination. In addition, the aforementioned methods are merely examples, and the plan of change may be generated using methods other than the aforementioned methods for generating a plan of change. It goes without saying that the number of plans of change to be generated can be arbitrarily set.

If either or both of 2 clinical pathways 26 are changed so as to avoid the overlap of the hospital resources between the clinical pathway 26 as a target of change and other clinical pathways 26, the hospital resources in the changed clinical pathway 26 and the hospital resources in still other clinical pathways 26 overlap with each other in some cases. The plans of change generated by the clinical pathway changing portion 56 also include plans by which 3 or more clinical pathways 26 are changed, such that all of the overlaps of the hospital resources that sequentially occur due to the change of a single clinical pathway 26 are avoided.

After the plurality of plans of change is generated as described above, the influence degree calculation portion 56D calculates a degree of influence of each of the plans of change. The degree of influence is a measure obtained by numerically expressing an extent of change made according to each of the plans of change. The influence degree calculation portion 56D calculates the degree of influence based on predetermined parameters.

In the present embodiment, as the parameters, the treatment costs that vary before and after the change made based on each of the plans of change and the number of patients of other clinical pathways 26 that are changed based on each of the plans of change are used. The number of patients of other clinical pathways 26 is the number of patients corresponding to the number of other clinical pathways 26 influenced by the change of the clinical pathway 26 as a target of change. Because the clinical pathway 26 is created for each patient, the number of other clinical pathways 26 in turn becomes the same as the number of patients of other clinical pathways 26.

Hereinafter, the method for calculating a degree of influence will be specifically described.

In the following section, an example will be described in which although "12-row multislice CT scanning (initial plan for the clinical pathway 26 as a target of change)" is scheduled in the current situation, the current clinical pathway 26 needs to be changed because, for example, the patient is late for the CT scanning due to a long distance or is unsuitable for undergoing CT scanning due to poor physical conditions, and the following 3 plans of change are generated in the process of the change.

[Plan of Change 1]

Sixty four-row multislice CT scanning (scheduled by changing the content of the initial plan, no change in other clinical pathways 26 (no patient influenced)) will be performed.

[Plan of Change 2]

Thirty two-row multislice CT scanning (scheduled by changing the content of the initial plan, number of other clinical pathways 26 changed: "1" (number of patients influenced: 1)) will be performed.

[Plan of Change 3]

Twelve-row multislice CT scanning (scheduled by changing the initially planned time, number of other clinical pathways 26 changed: "2" (number of patients influenced: 2)) will be performed.

In the current situation and in the state where the plans of change 1 to 3 are generated, the clinical pathway changing portion 56 calculates a degree of influence according to the following Equation 1 by using the treatment cost conversion table 30.

Degree of influence=[difference between treatment costs (points) after change and treatment costs (points) in current situation]+[number of patients influenced×500 (weighting coefficient)]     [Equation 1]

*The weighting coefficient can be set to be an arbitrary value.

Specifically, the treatment costs are "780 (points)" in the current situation, "950 (points)" in the plan of change 1, "900 (points)" in the plan of change 2, and "780 (points)" in the plan of change 3 (see FIG. 7). Furthermore, the number of patients influenced by the change is "0" in the plan of change 1, "1" in the plan of change 2, and "2" in the plan of change 2. Therefore, the degree of influence is "170" in the plan of change 1, "620" in the plan of change 2, and "1,000" in the plan of change 3.

After calculating the degree of influence as described above, the clinical pathway changing portion 56 selects the least influential plan of change (in the present embodiment, the plan of change 1) as a plan of change to be adopted, and then change the corresponding clinical pathway 26 according to the selected plan of change.

Figure 10:
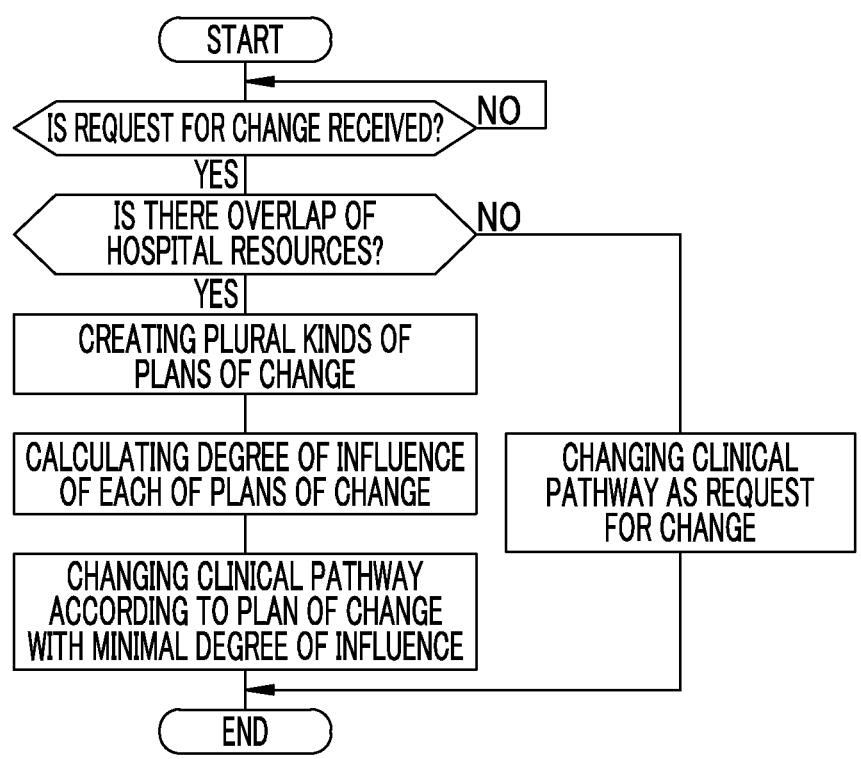
FIG. 10 is a flow chart showing a procedure of changing a clinical pathway.

Hereinafter, the operation of the present invention configured as above will be described based on the flowchart shown in FIG. 10. As shown in FIG. 10, in the clinical pathway management device 12, the reception portion 56A receives a request for change that requires the change of the content of the clinical pathway 26. With reference to the schedule data 29, the overlap determination portion 56B determines whether or not there is an overlap of hospital resources between the clinical pathway 26 as a target of change and other clinical pathways 26 in a case where the clinical pathway 26 is changed according to the request for change. In a case where there is no overlap, the clinical pathway changing portion 56 changes the clinical pathway 26 according to the request for change.

In contrast, in a case where there is an overlap of the hospital resources, by changing at least either the clinical pathway 26 as a target of change or other clinical pathways 26, the change plan generation portion 56C generates plural kinds of plans of change for avoiding the overlap. Subsequently, the influence degree calculation portion 56D calculates a degree of influence, which is a measure obtained by numerically expressing the extent of change made by each plan of change, for each of the plans of change. Then, the clinical pathway changing portion 56 compares the degrees of influence of the plurality of plans of change, automatically selects a plan of change with a minimal degree of influence from the plurality of plans of change, and changes the clinical pathway 26 according to the selected plan of change. The clinical pathway changing portion 56 functions as an automatic selection portion.

As described above, the clinical pathway management device 12 responds to the change of the clinical pathway as a target of change by changing other clinical pathways different from the clinical pathway as a target of change. Therefore, for example, even in a case where the change of only the clinical pathway as a target of change results in an overlap of hospital resources and thus clinical pathway cannot be changed, the clinical pathway can be changed by changing other clinical pathways. As a result, it is possible to flexibly change the clinical pathways.

Furthermore, in the clinical pathway management device 12, the clinical pathway is changed according to a plan of change, which is the least influential at the time of change, among a plurality of plans of change. Therefore, it is possible to prevent the problems in that other clinical pathways are changed more than necessary and thus leads to confusion.

The details of the configuration of the present invention are not limited to the embodiment described above and can be appropriately modified. For example, although the aforementioned embodiment was described by using an example in which the clinical pathway management device is installed in a company that operates a medical care support system, the clinical pathway management device may be installed in a medical institution to which the user of the medical care support system belongs.

The aforementioned embodiment was described by using an example in which a degree of influence is calculated using, as parameters, the treatment costs and the number of patients influenced. However, the specific method for calculating the degree of influence can be appropriately modified. For example, the degree of influence may be calculated using, as parameters, at least either the treatment costs or the number of patients influenced. Alternatively, the degree of influence may be calculated using new factors as parameters without using any of the treatment costs and the number of patients influenced as parameters. It goes without saying that the degree of influence may be calculated using a combination of two or more parameters including the treatment costs, the number of patients influenced, new factors described above, and the like.

Hereinafter, a method for calculating a degree of influence by using, as parameters, new factors different from the treatment costs or the number of patients influenced will be described using FIGS. 11 to 15.

First, an example in which a degree of influence calculated by using, as parameters, the number of medical staff influenced by the change, for instance, an example in which the operation schedule is forcedly changed due to the change of clinical pathways will be described using FIGS. 11 and 12.

In the present example, a degree of influence is calculated using a weighting correspondence table 110 shown in FIG. 11 and a weighting correspondence table 120 shown in FIG. 12. The weighting correspondence table 110 is established by associating the medical staff with weighting coefficients set for each of the types of the medical staff. In the example illustrated in FIG. 11, the medical staff is categorized into two types consisting of a doctor and a staff other than a doctor, and the type of the doctor and the type of the staff other than the doctor are further subdivided. The weighting correspondence table 120 is established by associating the levels of authority that each of the medical staff has with weighting coefficients set for each of the levels of authority. The weighting correspondence tables 110 and 120 are stored in, for example, the DB 18 (see FIGS. 1 and 2). The authority and type are attributes of the medical staff. As the attributes, either the authority or the type may be used, and the position or status other than the authority or type may be included in the attributes.

To summarize, in the present example, on a premise that a degree of influence may vary with the attributes of the medical staff, the degree of influence of a plan of change is calculated considering the attributes and number of medical staff to be changed.

In the present example, an example in which 2 plans of change consisting of the following plans of change 4 and 5 are generated will be described. In the description of the following plans of change, only the type of medical staff, whose operation schedule is changed in a case where the clinical pathway is changed according to each of the plans of change, and the authority level of the medical staff will be listed.

[Plan of Change 4]

The type of medical staff whose operation schedule is changed and the authority level of the medical staff: one surgeon (authority level 5) and five nurses (four with authority level 3 and one with authority level 1)

[Plan of Change 5]

The type of medical staff whose operation schedule is changed and the authority level of the medical staff: one radiologist (authority level 3) and three medical radiology technicians (all with authority level 2)

In the current situation described above and in a state where the plans of change 4 and 5 are generated, the clinical pathway changing portion 56 calculates a degree of influence according to the following Equation 2.

Degree of influence=[degree of influence of first medical staff whose operation schedule is changed (weighting coefficient according to the type of the medical staff (see FIG. 11)×weighting coefficient according to authority level of the medical staff (see FIG. 12))+[degree of influence of second medical staff whose operation schedule is changed]+ . . . (omission) . . . +[degree of influence of last medical staff whose operation schedule is changed]    [Equation 2]

Specifically, in the plan of change 4, the degree of influence=[10 (weighting coefficient corresponding to surgeon)×5 (authority level 5)]×1 (number of surgeon) (degree of influence of one surgeon with authority level of 5)+[6 (weighting coefficient corresponding to nurse)×3 (authority level 3)]×4 (number of nurses) (degree of influence of four nurses with authority level of 3)+[6 (weighting coefficient corresponding to nurse)×1 (authority level 1)]×1 (number of nurse) (degree of influence of one nurse with authority level of 1)=50 (degree of influence of one surgeon with authority level 5)+72 (degree of influence of four nurses with authority level 3)+6 (degree of influence of one nurse with authority level 1)=128.

In the plan of change 5, the degree of influence=[8 (weighting coefficient corresponding to radiologist)×3 (authority level 3)]×1 (number of radiologist) (degree of influence of one radiologist with authority level 3)+[4 (weighting coefficient corresponding to medical radiology technician)×3 (authority level 3)]×3 (number of medical radiology technicians) (degree of influence of three medical radiology technicians with authority level 3)=24 (degree of one radiologist with authority level 3)+36 (degree of influence of three medical radiology technicians with authority level 3)=60.

Therefore, in the present example, the plan of change 5 with a minimal degree of influence is selected as a plan of change to be adopted, and the corresponding clinical pathway 26 is changed according to the plan of change 5. In the present example, the degree of influence is calculated by performing weighting according to the type or authority level of the medical staff. However, the degree of influence may be calculated simply by adding up the number of medical staff whose operation schedules are changed when the current situation is changed to each of the plans of change, without performing weighting. It goes without saying that weighting may be performed for either the type or the authority level of the medical staff.

Next, an example in which a degree of influence is calculated using, as parameters, the number of medical instruments influenced by the change of the clinical pathway, for instance, an example in which the operation schedule is forcedly changed due to the change of the clinical pathway will be described using FIGS. 13 and 14.

To summarize, in the present example, on a premise that the degree of influence exerted on the medical instruments varies with the operation ratio, the degree of influence of the plan of change is calculated in consideration of the operation ratio of the medical instruments and the number of medical instruments to be changed.

In the present example, the degree of influence is calculated using a weighting correspondence table 130 shown in FIG. 13 and an operation ratio list 140 shown in Table 14. The weighting correspondence table 130 is established by associating the operation ratios of the medical instruments with weighting coefficients. The operation ratio list 140 is established by associating the types of the medical instruments with the operation ratios of the respective medical instruments, and stays up to date all the time by being updated with the updating (change) of the schedule data 29 (see FIG. 6). The weighting correspondence table 130 and the operation ratio list 140 are stored in, for example, the DB 18 (see FIGS. 1 and 2).

In the present example, a case where the following plans of change 6 and 7 are generated in a state where the operation ratios of medical instruments are as shown in FIG. 14 will be described. In the description of the following plans of change, only the medical instruments whose operation schedule is changed in a case where the clinical pathway is changed according to each of the plans of change and the number of times of the change are listed. The number of times of the change means the number of times the operation schedule for a single medical instrument is changed. For example, if the date and time when a medical instrument in a single clinical pathway 26 is to be operated are changed, a change is added to the operation schedule. In this case, the counted number of times of the change is 1. Furthermore, in a case where other clinical pathways 26 are changed, other changes are further added to the operation schedule accordingly, and hence the number of times of the change increases by 1 and becomes 2 in total.

[Plan of Change 6]
The medical instruments whose operation schedule is changed and the number of times of the change
CT: number of times of change of operation schedule=4
MRI: number of times of change of operation schedule=3

[Plan of Change 7]
The medical instruments whose operation schedule is changed and the number of times of the change
Mammography: number of times of change of operation schedule=2
Ultrasonograph: number of times of change of operation schedule=10

In the current situation described above and in the state where the plans of change 6 and 7 are generated, the clinical pathway changing portion 56 calculates a degree of influence according to Equation 3.

Degree of influence=[degree of influence of first medical instrument whose operation schedule is changed (weighting coefficient corresponding to the operation ratio of the medical instrument)]+ [number of times of change of second medical instrument whose operation schedule is changed]+ . . . (omission) . . . +[number of time of change of last medical instrument whose operation schedule is changed]    [Equation 3]

Specifically, in the plan of change 6, the degree of influence=[4 (weighting coefficient corresponding to the operation ratio of CT)×4 (times) (number of times of change of CT)+[5 (weight coefficient corresponding to the operation ratio of MRI)]×3 (times) (number of times of change of MRI)=16 (degree of influence resulting from change of CT occurring 4 times)+15 (degree of influence resulting from change of MRI occurring 3 times)=31.

In the plan of change 7, the degree of influence=[3 (weighting coefficient corresponding to the operation ratio of mammography)]×2 (times) (number of times of change of mammography)+[3 (weighting coefficient corresponding to the operation ratio of ultrasonograph)]×10 (times) (number of times of change of the ultrasonograph)=6 (degree of influence resulting from the change of the mammography occurring 2 times)+30 (degree of influence resulting from the change of the ultrasonograph occurring 10 times)=36.

Therefore, in the present example, the plan of change 6 with a minimal degree of influence is determined as a plan of change to be adopted, and according to the plan of change 6, the corresponding clinical pathway 26 is changed. In the present example, an example in which image examination devices are used as the medical instruments was described. However, the degree of influence may be calculated using the operation ratio of other medical instruments as parameters. Furthermore, in the present example, weighting is performed based on the operation ratio. However, the degree of influence may be calculated simply by adding up the number of medical instruments whose operation schedules are changed when the current situation is changed to each of the plans of change or by adding up the number of times of the change of the operation schedule, without performing weighting.

In addition, the weighting coefficients which correspond not to the operation ratios of the medical instruments but to the types of the medical instruments may be set, and the degree of influence may be calculated using the weighting coefficients corresponding to the types in addition to the weighting coefficients of the operation ratios or using only the weighting coefficients corresponding to the types.

Hitherto, an example in which the treatment costs and the number of patients influenced are used as parameters, an example in which the number of medical staff whose operation schedules are changed are used as parameters (including the configuration in which weighting is performed based on the types or authority levels of the medical staff when values used as parameters are generated), and an example in which the number of medical instruments whose operation schedules are changed or the number of times of the change is used as parameters (including the configuration in which weighting is performed based on the operation ratios of the medical instruments when values used as parameters are generated) have been described. Lastly, by using FIG. 15, an example will be described in which a degree of comprehensive influence as a degree of overall influence is calculated using the techniques for calculating the degree of influence described above in combination. Hereinafter, the degree of influence of each of the aforementioned techniques will be referred to as a degree of individual influence such that it is distinguished from the degree of comprehensive influence.

In the present example, the degree of comprehensive influence is calculated using a weighting correspondence table 150 shown in FIG. 15. The weighting correspondence table 150 is established by associating items of change (types of parameters) with weighting coefficient. The weighting correspondence table 150 is stored in, for example, the DB 18 (see FIGS. 1 and 2).

In FIG. 15, the change of treatment content represents a technique (technique 1) for calculating a degree of individual influence by using parameters changed with the change of the treatment content, and specifically includes a technique for calculating a degree of individual influence by using, as parameters, the treatment costs or the number of patients influenced. Furthermore, the change of staff represents a technique (technique 2) for calculating a degree of individual influence by using parameters changing with the change of the medical staff, and specifically includes a technique for calculating a degree of individual influence by using, as parameters, the number of medical staff whose schedules are changed. In addition, the change of medical instruments represents a technique (technique 3) for calculating a degree of individual influence by using parameters changing with the change of the medical instruments, and specifically includes a technique for calculating a degree of individual influence by using, as parameters, the number of medical instruments whose schedules are changed or the number of times of the change.

In the present example, if a plan of change is generated, a degree of individual influence of the generated plan of change is calculated by the three techniques 1 to 3 consisting of the change of treatment content, the change of staff, and the change of medical instruments. Even in the same plan of change, the evaluation criteria vary with the technique for calculating the degree of individual influence, and hence the value of the degree of individual influence varies. The degree of individual influence calculated by each of the techniques 1 to 3 is categorized into any of levels of a plurality of stages (for example, 10 stages) according to the degree of individual influence.

For example, if the "plan of change 1" described above is generated, for the generated "plan of change 1", a degree of individual influence is calculated by the technique 1 (change of treatment content) (in this case, treatment costs (780 points) of current situation−treatment costs (950 points) of "plan of change 1"="170 points" are calculated as a degree of influence) (see FIG. 7). Then, by determining into which level the calculated degree of individual influence ("170 (points)" in this case) is categorized among the 10 stages, the calculated degree of individual influence is categorized into, for example, "level 5 (fifth stage)".

Likewise, by the technique 2 (change of medical staff), the degree of individual influence of the "plan of change 1" is calculated (see FIGS. 11 and 12), and the degree of individual influence is categorized into any of the 10 stages such that it is categorized into, for example, the "level 3 (third stage)". Furthermore, by the technique 3 (change of medical instrument), the degree of individual influence of "plan of change 1" is calculated (see FIGS. 13 and 14), and the degree of individual influence is categorized into any of the 10 stages such that it is categorized into, for example, the "level 7 (seventh stage)".

In this way, for a single plan of change, 3 kinds of degrees of influence are calculated by the three techniques 1 to 3, and the three kinds of degrees of influences are categorized into any of the 10 stages respectively. For example, in the "plan of change 1", the degree of individual influence from the technique 1 (change of treatment content) is categorized into the "level 5 (fifth stage)"; the degree of individual influence from the technique 2 (change of medical staff) is categorized into the "level 3 (third stage)"; and the degree of individual influence from the technique 3 (change of medical instrument) is categorized into the "level 7 (seventh stage)".

After the categorization is finished, a degree of comprehensive influence is calculated by the following Equation 4.

$$\text{Degree of comprehensive influence} = [\text{level into which the value of degree of individual influence of technique 1 (change of treatment content) is categorized}] \times [\text{corresponding weighting coefficient}] + [\text{level into which the value of degree of individual influence of technique 2 (change of medical staff) is categorized}] \times [\text{corresponding weighting coefficient}] + [\text{level into which the value of degree of individual influence of technique 3 (change of medical instrument)}] \times [\text{corresponding coefficient}] \quad [\text{Equation 4}]$$

For example, in the "plan of change 1", in a case where the value of the degree of individual influence of the technique 1 (change of treatment content) is categorized into the "level 5 (fifth stage)"; the degree of individual influence of the technique 2 (change of medical staff) is categorized into the "level 3 (third stage)"; and the degree of individual influence of the technique 3 (change of medical instrument) is categorized into the "level 7 (seventh stage)", the degree of comprehensive influence=[level 5]×[5 (weighting coefficient)]+[level 3]×[4 (weighting coefficient)]+[level 7]×[3 (weighting coefficient)]=25+12+21=58.

For other plans of change, the degree of individual influence of each technique is calculated according to the same procedure as described above, and based on the degree of individual influence, a degree of comprehensive influence is calculated. After the degrees of comprehensive influence of all of the plans of change are calculated, according to a plan of change with a minimal degree of comprehensive influence, the clinical pathway 26 is changed.

The above techniques 1 to 3 were described using an example in which the techniques include different parameters respectively. However, the degree of individual influence may be calculated by a technique other than the techniques 1 to 3 that includes parameters partially different from those of the techniques 1 to 3. Furthermore, the number of techniques calculating the degree of individual influence is not limited to 3, and may be 2 or equal to or greater than 4. In addition, the content of the technique for calculating the degree of individual influence, that is, the type or number of the parameters included in each of the techniques may be appropriately changed.

Hitherto, regarding the specific method for calculating the degree of influence, various methods have been described. However, the method for calculating the degree of influence is not limited to the aforementioned methods, and other appropriate methods can also be used.

In the above embodiment, an example was described in which the clinical pathway management device automatically changes clinical pathways according to a change of plan with a minimal degree of influence. However, the plan of change or the degree of influence of each the plans of change may be reported to a user by being delivered to the user's terminal, and the user may be allowed to determine which of the plans of change is to be adopted. In this case, the CPU 36 of the clinical pathway management device functions as a manual selection portion which delivers a plan selection screen for allowing the user to select a plan of change to the user's terminal and receives information about the plan of change selected through the plan selection screen. The plan selection screen includes the content of the plan of change and the degree of influence.

In the above embodiment, an example was described in which the clinical pathway is changed when the request for change is sent from the user's terminal. However, the clinical pathway management device may automatically change the clinical pathway. In this case, the clinical pathway management device detects the current position of the user by using, for example, a GSP system, and determines whether or not the user can reach the place where a treatment is performed at the time when the treatment is to be performed by checking the detected current position of the user against the schedule data. In a case where it is determined that the user cannot reach the place where the treatment is performed at the time when the treatment is to be to performed, the clinical pathway should be changed according to the same procedure as described above (procedure in which the clinical pathway is changed when the request for change is sent).

In the above embodiment, an example was described in which the present invention is applied to a case where the clinical pathway that has already been created is to be changed. However, the present invention may be applied when a new clinical pathway is created. In this case, based on a request for generation of a new clinical pathway, plural kinds of plans of creation including change of other clinical pathways should be generated, a degree of influence that each of the plans of creation exerts on other clinical pathways should be calculated, and a new clinical pathway should be created according to a plan of creation plan with a minimal degree of influence.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A clinical pathway management device comprising:
    a database storing a plurality of clinical pathways showing treatment plans for each patient and schedule data showing operation schedules of hospital resources including at least either human resources or material resources that are assigned to each treatment in each of the clinical pathways; and
    a processor configured to:
    receive a request for change that requires the change of at least either content of the treatment in the clinical pathways or date and time of performing the treatment in the clinical pathways;
    determine whether or not there is an overlap between the hospital resources assigned to a treatment included in a clinical pathway as a target of change and the hospital resources assigned to a treatment included in other clinical pathways different from the clinical pathway as the target of change in a case where the clinical pathway as the target of change is changed according to the request for change;
    generate, in a case where there is an overlap, plural kinds of plans of change for avoiding the overlap by changing at least either the clinical pathway as the target of change or other clinical pathways;
    calculate a degree of influence numerically expressing an extent of change made according to each of the plural kinds of plans of change, wherein the calculation of the degree of influence is a numerical calculation based on parameters, and the parameters include the number and/or type of the hospital resources;
    determine a position of user via a global positioning system in order to determine whether or not the user can reach the place where the treatment is to be performed; and
    change the clinical pathways, wherein in a case where there is no overlap described above, and when it is determined that the user can reach the place where treatment is to be performed, the processor changes the clinical pathways according to the request for change, and in a case where there is the overlap, the processor changes the clinical pathways according to a plan of change determined based on the degree of influence.

2. The clinical pathway management device according to claim 1, wherein the processor is further configured to:
    select a plan of change with a minimal degree of influence by comparing degrees of influence of the respective plans of change,
    wherein the processor changes the clinical pathways according to the selected plan of change.

3. The clinical pathway management device according to claim 1, wherein the processor is further configured to:
    allow a user to determine which of the plans of change is to be adopted by delivering a plan selection screen including the content of each of the plans of change and a degree of influence of each of the plans of change to a terminal of the user,
    wherein the processor changes the clinical pathways according to a plan of change selected by the user.

4. The clinical pathway management device according to claim 1,
    wherein the parameters include treatment costs that change with the change of the clinical pathways.

5. The clinical pathway management device according to claim 1,
    wherein the parameters include the number of patients of other clinical pathways influenced by the change of the clinical pathway as the target of change.

6. The clinical pathway management device according to claim 1,
    wherein the parameters include the number of medical staff as the human resources influenced by the change of the clinical pathways.

7. The clinical pathway management device according to claim 6,
    wherein weighting coefficients for performing weighting according to attributes of the medical staff to be changed are set, and
    the processor calculates the degree of influence based on the number of the medical staff and the weighting coefficients corresponding to the attributes.

8. The clinical pathway management device according to claim 1, wherein the parameters include the number of medical instruments as the material resources influenced by the change of the clinical pathways.

9. The clinical pathway management device according to claim 8, wherein weighting coefficients for performing weighting according to operation ratios of the medical instruments are set, and the processor calculates the degree of influence based on the number of medical instruments and the weighting coefficients corresponding to the operation ratios.

10. The clinical pathway management device according to claim 1, wherein the parameters are stored and the processor calculates the degree of influence as a degree of individual influence of each technique by using a plurality of techniques different from each other in terms of at least one of the parameters, weighting coefficients for performing weighting according to the techniques are set, and the processor calculates a degree of comprehensive influence based on the degree of individual influence of each of the techniques and the weighting coefficients of each of the techniques.

* * * * *